(12) United States Patent
Hepworth et al.

(10) Patent No.: US 11,844,374 B2
(45) Date of Patent: Dec. 19, 2023

(54) AEROSOL PROVISION SYSTEMS

(71) Applicant: NICOVENTURES TRADING LIMITED, London (GB)

(72) Inventors: Richard Hepworth, London (GB); Patrick Moloney, London (GB); Colin Dickens, London (GB)

(73) Assignee: Nicoventures Trading Limited, London (GB)

( * ) Notice: Subject to any disclaimer, the term of this patent is extended or adjusted under 35 U.S.C. 154(b) by 841 days.

(21) Appl. No.: 16/754,500

(22) PCT Filed: Oct. 11, 2018

(86) PCT No.: PCT/GB2018/052910
§ 371 (c)(1),
(2) Date: Apr. 8, 2020

(87) PCT Pub. No.: WO2019/073237
PCT Pub. Date: Apr. 18, 2019

(65) Prior Publication Data
US 2020/0390149 A1    Dec. 17, 2020

(30) Foreign Application Priority Data

Oct. 12, 2017  (GB) ...................................... 1716735

(51) Int. Cl.
*A24F 40/20*      (2020.01)
*A24F 40/46*      (2020.01)
(Continued)

(52) U.S. Cl.
CPC .............. *A24F 40/20* (2020.01); *A24F 40/42* (2020.01); *A24F 40/46* (2020.01); *A24F 40/465* (2020.01); *A24F 40/10* (2020.01); *A24F 40/30* (2020.01)

(58) Field of Classification Search
None
See application file for complete search history.

(56) References Cited

U.S. PATENT DOCUMENTS 11,596,751 B2 *   3/2023   Potter .................. H01R 31/065
2008/0110454 A1   5/2008   White et al.
(Continued)

FOREIGN PATENT DOCUMENTS

CN       103960784 A    8/2014
CN       204169043 U    2/2015
(Continued)

OTHER PUBLICATIONS

Examination Report received for Australian Patent Application No. 2018347774, dated Dec. 16, 2020, 4 Pages.
(Continued)

*Primary Examiner* — James Harvey
(74) *Attorney, Agent, or Firm* — Patterson Thuente P.A.

(57) ABSTRACT

A consumable component for an aerosol provision system includes an outer housing including an outer wall extending between first and second end walls to define an interior chamber; a plurality of elements of solid aerosol forming material for generating an aerosol for user inhalation, wherein the plurality of elements of solid aerosol forming material are retained within the interior chamber by the housing and wherein the first and second end walls comprise openings to allow air to flow into the interior chamber through the first end wall and out of the interior chamber through the second end wall during use, and a heater located within the interior chamber and configured to heat the elements of solid aerosol forming material during use to generate a vapor for user inhalation.

19 Claims, 6 Drawing Sheets

(51) Int. Cl.
*A24F 40/465* (2020.01)
*A24F 40/42* (2020.01)
*A24F 40/10* (2020.01)
*A24F 40/30* (2020.01)

(56) References Cited

U.S. PATENT DOCUMENTS

| | | |
|---|---|---|
| 2012/0312314 A1 | 12/2012 | Plakidis et al. |
| 2014/0345606 A1 | 11/2014 | Talon |
| 2015/0101606 A1 | 4/2015 | White |
| 2015/0208729 A1 | 7/2015 | Monsees et al. |
| 2015/0209530 A1 | 7/2015 | White |
| 2015/0320116 A1 | 11/2015 | Bleloch et al. |
| 2016/0295921 A1 | 10/2016 | Mironov et al. |
| 2017/0258132 A1 | 9/2017 | Rostami et al. |
| 2018/0117268 A1* | 5/2018 | Selby .................. A61M 15/06 |
| 2019/0174832 A1* | 6/2019 | Lin ...................... A61M 15/06 |
| 2020/0114095 A1* | 4/2020 | Holroyd ............. A61M 15/003 |
| 2020/0390149 A1* | 12/2020 | Hepworth ................. A24F 1/00 |

FOREIGN PATENT DOCUMENTS

| | | |
|---|---|---|
| CN | 104382224 A | 3/2015 |
| CN | 104957777 A | 10/2015 |
| CN | 105581378 A | 5/2016 |
| CN | 105686060 A | 6/2016 |
| CN | 205658376 U | 10/2016 |
| CN | 206227716 U | 6/2017 |
| EP | 3251529 A1 | 12/2017 |
| JP | 2015512262 A | 4/2015 |
| JP | 2016525341 A | 8/2016 |
| JP | 6001201 B1 | 10/2016 |
| JP | 2016532432 A | 10/2016 |
| RU | 2268631 C2 | 1/2006 |
| RU | 2606866 C1 | 1/2017 |
| WO | 9527411 A1 | 10/1995 |
| WO | 03056949 A1 | 7/2003 |
| WO | 2008029381 A2 | 3/2008 |
| WO | 2013148810 A1 | 10/2013 |
| WO | 2015140554 A1 | 9/2015 |
| WO | 2015177253 A1 | 11/2015 |
| WO | 2015177264 A1 | 11/2015 |
| WO | 2016062786 A1 | 4/2016 |
| WO | 2016135331 A1 | 9/2016 |
| WO | 2016135959 A1 | 9/2016 |
| WO | 2016156609 A1 | 10/2016 |
| WO | 2016174179 A1 | 11/2016 |
| WO | 2017055795 A1 | 4/2017 |
| WO | 2017089939 A1 | 6/2017 |

OTHER PUBLICATIONS

Examination Report received for Japanese Patent Application No. 2020-518810, dated Jan. 24, 2023, 11 pages (6 pages of English Translation and 5 pages of Official copy).
International Preliminary Report on Patentability received for PCT Patent Application No. PCT/GB2018/052910, dated Apr. 23, 2020, 7 Pages.
International Search Report and Written Opinion received for PCT Patent Application No. PCT/GB2018/052910, dated Jan. 4, 2019, 9 Pages.
Notice of Reasons for Rejection received for Japanese Patent Application No. 2020-518810, dated Nov. 24, 2021, 10 Pages (5 Pages of English Translation and 5 Pages of Official Copy).
Notice of Reasons for Rejection received for Japanese Patent Application No. 2020-518810, dated Mar. 30, 2021, 9 Pages (4 Pages of English Translation and 5 Pages of Official Copy).
Office Action received for Canadian Patent Application No. 3078860, dated Aug. 5, 2022, 7 Pages.
Office Action received for Canadian Patent Application No. 3078860, dated Feb. 2, 2023, 7 Pages.
Office Action received for Canadian Patent Application No. 3078860, dated May 26, 2021, 7 Pages.
Office Action received for Chinese Patent Application No. 2018800662709, dated Apr. 25, 2022, 17 pages (8 pages of English Translation and 9 pages of Official Copy).
Office Action received for European Patent Application No. 18788844. 1, dated Dec. 14, 2022, 5 Pages.
Search Report received for Russian Patent Application No. 2020112258, completed on Jul. 13, 2020, 2 pages.

* cited by examiner

AEROSOL PROVISION SYSTEMS

PRIORITY CLAIM

The present application is a National Phase entry of PCT Application No. PCT/GB2018/052910, filed Oct. 11, 2018, which claims priority from GB Patent Application No. 1716735.4, filed Oct. 12, 2017, each which is hereby fully incorporated herein by reference.

FIELD

The present disclosure relates to aerosol provision systems such as nicotine delivery systems (e.g. electronic cigarettes and the like).

BACKGROUND

Electronic aerosol provision systems such as electronic cigarettes (e-cigarettes) generally contain an aerosol precursor material, such as a reservoir of a source liquid containing a formulation, typically including nicotine, or a solid material such a tobacco-based product, from which an aerosol is generated for inhalation by a user, for example through heat vaporization. Thus, an aerosol provision system will typically comprise a heater arranged to vaporize a portion of aerosol precursor material to generate a vapor/aerosol in a flow path extending through the electronic aerosol provision system from an air inlet to an aerosol outlet. As a user inhales on the aerosol outlet and electrical power is supplied to the vaporizer, air is drawn in through the air inlet, along the flow path where the air mixes with vaporized precursor material and forms a condensation aerosol, and continues along the flow path to the aerosol outlet, carrying the condensation aerosol with it, from where it may be inhaled by the user.

SUMMARY

According to a first aspect of certain embodiments there is provided a consumable component for an aerosol provision system comprising: an outer housing comprising an outer wall extending between first and second end walls to define an interior chamber; a plurality of elements of solid aerosol forming material for generating an aerosol for user inhalation when heated, wherein the plurality of elements of solid aerosol forming material are retained within the interior chamber by the housing and wherein the first and second end walls comprise openings to allow air to flow into the interior chamber through the first end wall and out of the interior chamber through the second end wall during use, and a heater located within the interior chamber and configured to heat the elements of solid aerosol forming material during use to generate a vapor for user inhalation.

According to another aspect of certain embodiments there is provided an aerosol provision system for generating a vapor using a consumable component, wherein the consumable component comprises an outer housing comprising an outer wall extending between first and second end walls to define an interior chamber; a plurality of elements of solid aerosol forming material for generating an aerosol for user inhalation when heated, wherein the plurality of elements of solid aerosol forming material are retained within the interior chamber by the housing and wherein the first and second end walls comprise openings to allow air to flow into the interior chamber through the first end wall and out of the interior chamber through the second end wall during use, and a heater located within the interior chamber and configured to heat the elements of solid aerosol forming material during use to generate a vapor for user inhalation, and the wherein the aerosol provision system comprises: the consumable component; a consumable component receiving section for removably receiving the consumable component for use; and a power source for selectively supplying power to the heater in the consumable component to generate vapor from the solid aerosol forming material for user inhalation.

According to another aspect of certain embodiments there is provided consumable component means for an aerosol provision system comprising: outer housing means comprising outer wall means extending between first and second end wall means to define an interior chamber; a plurality of elements of solid aerosol forming means for generating an aerosol for user inhalation when heated, wherein the plurality of elements of solid aerosol forming means are retained within the interior chamber by the housing means and wherein the first and second end wall means comprise opening means to allow air to flow into the interior chamber through the first end wall means and out of the interior chamber through the second end wall means during use, and heater means located within the interior chamber and configured to heat the elements of solid aerosol forming means during use to generate a vapor for user inhalation.

It will be appreciated that features and aspects of the disclosure described above in relation to the first and other aspects of the invention are equally applicable to, and may be combined with, embodiments of the disclosure according to other aspects of the disclosure as appropriate, and not just in the specific combinations described above.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to vapor provision systems, which may also be referred to as aerosol provision systems, such as e-cigarettes. Throughout the following description the term "e-cigarette" or "electronic cigarette" may sometimes be used; however, it will be appreciated this term may be used interchangeably with vapor (aerosol) provision system and electronic vapor (aerosol) provision system. Furthermore, and as is common in the technical field, the terms "vapor" and "aerosol", and related terms such as "vaporize" and "aerosolize", may also be used interchangeably.

Aerosol provision systems in accordance with certain embodiment of the disclosure may comprise a modular assembly including both a reusable part and a replaceable cartridge part, which may also be referred to as a consumable component of the system. For modular systems that use a liquid aerosol precursor material, the reusable device part will typically comprise the power supply and control circuitry. The consumable component (i.e. the replaceable/disposable part) may typically comprise the vapor precursor material and the vaporizer (e.g. often a heating coil wound around a wick). For modular systems that use a solid aerosol precursor material, the reusable device part will typically comprise the power supply, control circuitry and vaporizer (e.g. a heating oven) and the consumable component will typically comprise the vapor precursor material.

Figure 1:
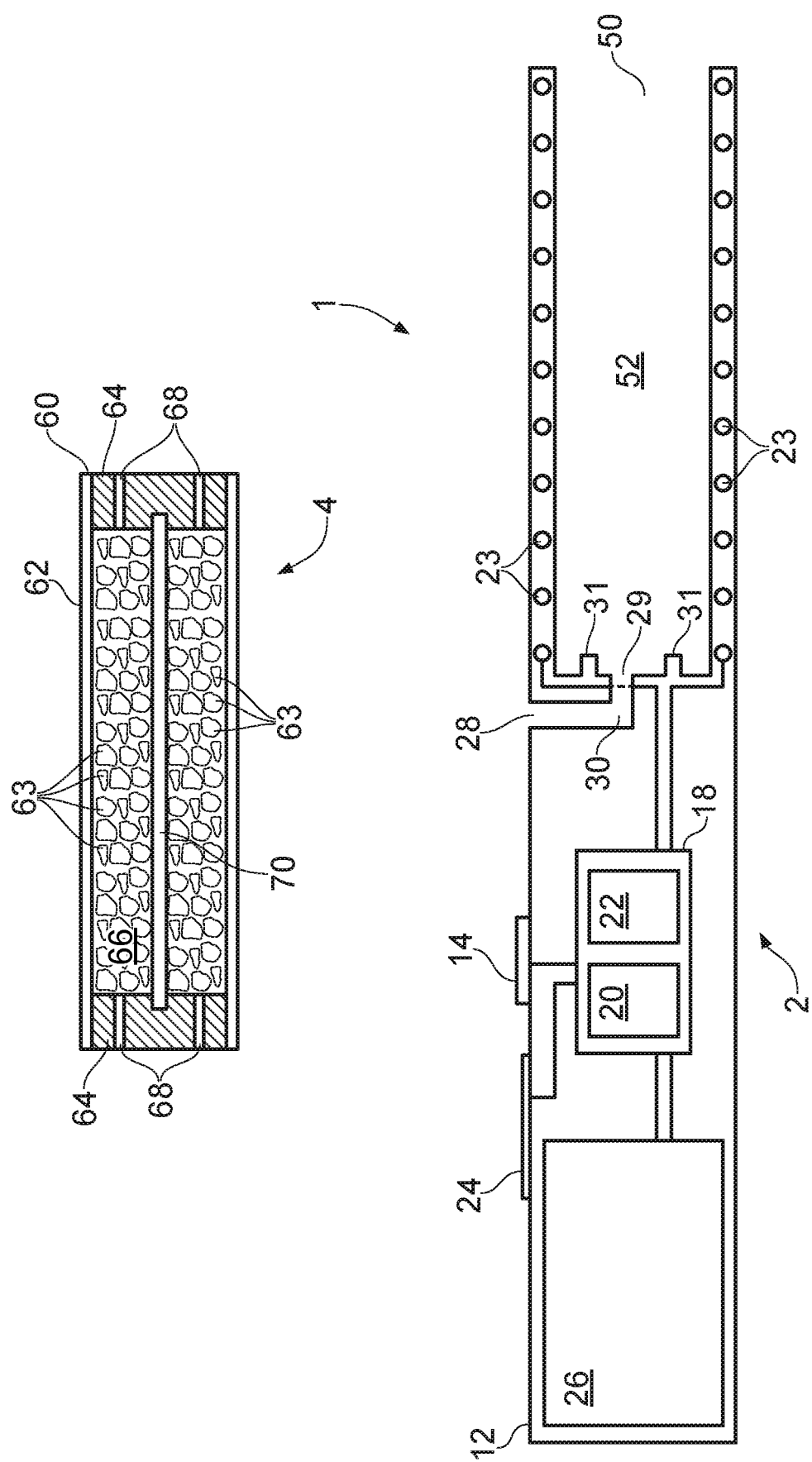
FIG. 1 is a section view of an aerosol provision system comprising a device part and a consumable component in accordance with certain embodiments of the disclosure.

FIG. 1 is a cross-sectional view through an example e-cigarette 1 in accordance with certain embodiments of the disclosure. The e-cigarette 1 comprises two main components, namely a reusable (device) part 2 and a consumable component 4. The consumable component may also be referred to as a replaceable/disposable cartridge part. The reusable part 2 and the consumable component 4 are shown separately in FIG. 1, but in normal use the consumable component 4 is placed in a consumable component receiving zone 52 of the reusable part 2. The consumable component receiving zone 52 is in effect an opening/receptacle which is dimensioned to receive the consumable component for use. The consumable component may be retained in the consumable component receiving zone by a friction fit or other means, such as a releasable latch or clip, so that it can be withdrawn from the reusable part and replaced with another when it is exhausted or the user wishes to change to a different consumable component, for example to change flavor. The specific manner in which the consumable component is retained in the reusable part during use is not of primary significance to the principles described herein.

The reusable part 2 in this example comprises a battery 26 for providing operating power for the electronic cigarette, control circuitry 18 for controlling and monitoring the operation of the electronic cigarette, a user input button 14 and a visual display 24.

The outer housing 12 may be formed, for example, from a plastics or metallic material and in this example has a generally circular cross section with a diameter of around 1.5 cm and a length of around 12 cm. However, it will be appreciated the overall shape and scale of electronic cigarettes according to different embodiments of the disclosure are not of primary significance to the principles described herein. For example, in some implementations the electronic cigarette may have a significantly larger size, for example to accommodate a larger battery to provide for longer use between charges.

The outer housing 12 defines an opening 50 for the consumable component receiving zone 52 at one end of the electronic cigarette 1 through which the consumable component 4 may be inserted into the consumable component receiving zone for use. In this example the receiving zone 52 has a diameter of around 1 cm and a length of around 4 cm (i.e. the outer housing defines a wall around the consumable component receiving zone having a thickness of around 2.5 mm). The opening 50 at the end of the electronic cigarette 1 may be referred to as a mouthpiece opening, and it is through this mouthpiece opening 50 that aerosol generated by the electronic cigarette 1 during use is inhaled by a user. In some examples the electronic cigarette 1 may further comprise an additional mouthpiece cap which is fitted to the mouthpiece opening end of the electronic cigarette and which tapers to a profile for comfortable placement between a user's lips.

The outer housing 12 has an air inlet 28 connected to an air path 30 through the reusable part 2. The air path 30 opens to the consumable component receiving zone at a consumable component receiving zone air inlet 29. Thus, when a user inhales on the mouthpiece opening 50 (or a mouthpiece attached thereto), air is drawn in through the air inlet 28, along the reusable part air path 30, through the consumable component receiving zone air inlet 29 and into the consumable component receiving zone 52. The air continues through the consumable component receiving zone 52 (and more particularly through a consumable component located in the consumable component receiving zone 52 during use) and out through the mouthpiece opening 50 for user inhalation. A surface of consumable component receiving zone around the consumable component receiving zone air inlet 29 includes spacers 31 (e.g. in the form of molded projections) to ensure the consumable component remains offset from the receiving zone air inlet 29 when located in the consumable component receiving zone 52 to avoid it blocking the receiving zone air inlet 29. Other configurations may not include such spacers 31, but may include other means to avoid blocking the consumable component receiving zone air inlet 29, the example air inlets for the consumable component may be arranged to align with the consumable component receiving zone air inlet when the consumable component is located in the consumable component receiving zone.

The battery 26 in this example is rechargeable and may be of a conventional type, for example of the kind normally used in electronic cigarettes and other applications requiring provision of relatively high currents over relatively short periods. The battery 26 may be recharged through a charging connector in the reusable part housing 12, for example a USB connector.

The user input button 14 in this example is a conventional mechanical button, for example comprising a sprung mounted component which may be pressed by a user to establish an electrical contact. However, the specific manner in which the button is implemented is not significant. For example, other forms of mechanical button(s) or touch-sensitive button(s) (e.g. based on capacitive or optical sensing techniques) may be used in other implementations.

The display 24 is provided to give a user a visual indication of various characteristics associated with the electronic cigarette, for example current power setting information, remaining battery power, and so forth. The display may be implemented in various ways. In this example the display 24 comprises a conventional pixilated LCD screen that may be driven to display the desired information in accordance with conventional techniques. In other implementations the display may comprise one or more discrete indicators, for example LEDs, that are arranged to display the desired information, for example through particular colors and/or flash sequences. More generally, the manner in which the display is provided and information is displayed to a user using the display is not significant to the principles described herein. For example some embodiment may not include a visual display and may include other means for providing a user with information relating to operating characteristics of the electronic cigarette, for example using audio signaling, or may not include any means for providing a user with information relating to operating characteristics of the electronic cigarette.

The control circuitry 18 is suitably configured/programmed to control the operation of the electronic cigarette to provide functionality in accordance with embodiments of the disclosure as described further herein, as well as for providing conventional operating functions of the electronic cigarette in line with the established techniques for controlling such devices. The control circuitry (processor circuitry) 18 may be considered to logically comprise various sub-units/circuitry elements associated with different aspects of the electronic cigarette's operation. In this example the control circuitry 18 comprises power supply control circuitry 22 for controlling a supply of power to a consumable component for vapor generation as discussed further herein in response to user input (e.g. using input button 14 or other means, such as an inhalation detector), user programming circuitry 20 for establishing configuration settings (e.g. user-defined power settings) in response to user input (e.g. using input button 14 or other means, such as a connected computer), as well as other functional units/circuitry associated functionality in accordance with the principles described herein and conventional operating aspects of electronic cigarettes, such as display driving circuitry and user input detection circuitry. It will be appreciated the functionality of the control circuitry 18 can be provided in various different ways, for example using one or more suitably programmed programmable computer(s) and/or one or more suitably configured application-specific integrated circuit(s)/circuitry/chip(s)/chipset(s) configured to provide the desired functionality.

For the example implementation represented in FIG. 1, power is supplied to the consumable component for vapor generation using electromagnetic induction. Accordingly, the power supply control circuitry 22 is configured to drive an induction heating coil 23 surrounding the consumable component receiving zone 52.

Turning now to the consumable component 4 represented in FIG. 1, this comprises an outer housing 60 comprising an outer wall 62 extending between first and second end walls 64 to define an interior chamber 66. The consumable component 4 is dimensioned so that it may be received with a friction fit in the receiving zone 52 of the reusable part 1. Thus in this example the consumable component 4 is generally cylindrical with a diameter of around 1 cm (corresponding to the 1 cm diameter of the receiving zone) and a length of around 4 cm. In some examples the consumable component may be slightly longer than the receiving zone so that an end of the consumable component protrudes from the consumable component receiving zone to facilitate its removal from the receiving zone. In other examples the consumable component may have a sufficiently loose friction fit in the receiving zone that it may be shaken free for removal. In yet other examples there may be different arrangements provided to facilitate removal of the consumable component from the receiving zone. For example, in some cases a slider or plunger based ejection mechanism may be provided which engages with the consumable component when located in the receiving zone 52 so that it may be mechanically ejected. More generally, the specific manner in which the consumable component is inserted into and removed from the receiving zone is not of primary significance to the principles described herein.

The outer wall 62 and/or the end walls 64 of the outer housing 60 may be at least partially formed from any one of a paper material, a card material, a tobacco material (for example a compressed tobacco industry by-product such as compressed tobacco fibers, tobacco stems or tobacco particles), a ceramic material, a metallic material, a carbon material, and a plastics material, or a combination thereof. In the example of FIG. 1, it is assumed the outer wall 62 is formed from wrapped paper and the end walls 64 are formed from a ceramic material. The outer wall 62 defines a cylinder and the end wall 64 comprises friction fit plugs inserted into respective ends of the cylinder defined by the outer wall 62. The end walls may, for example, have a diameter corresponding to the diameter of the outer wall 62 and have a thickness on of around 3 mm to 5 mm or so. The end walls 64 further comprise openings 68 through which air can enter and exit the inner chamber 66.

The interior chamber 66 of the consumable component 4 contains a plurality of fragments (e.g. granules) of solid aerosol forming material 63 for generating an aerosol for user inhalation when heated. In this example the fragments/elements of solid aerosol forming material comprise an absorbent solid substrate material, e.g. calcium carbonate or carbon, holding a liquid aerosol precursor material, for example a liquid of the kind conventionally used for vapor generation in electronic cigarettes, e.g. a liquid based on glycerol (polypropylene glycol (PG), triacetin, and/or other humectants) and containing additives such as nicotine and/or flavorings. In some examples the fragments of solid aerosol forming material may comprise tobacco, for example shredded/cut tobacco, with or without a liquid aerosol precursor material absorbed therein. The fragments of solid aerosol forming material may, for example, have an average characteristics dimension of at least 1 mm and less than 5 mm, 4 mm or 3 mm. The average characteristics dimension may, for example, be a minimum dimension or a mean dimension for each fragment. The fragments of solid aerosol forming material may be loosely packed in the interior chamber of the consumable component so that gaps remain between the fragments to allow air to be drawn through the consumable component during use. The fragments of the aerosol forming material may have various shapes, for example, they may be irregular (e.g. formed by cruching/grinding a larger block of material or cutting tobacco leaf) or regular, for example formed by extrusion of a suitable material. The fragments of solid aerosol forming material are retained in the interior chamber by the outer wall 62 and the end walls 64. In this regard the openings 68 in the end walls 64 through which air can enter and exit the inner chamber 66 may have a size selected to reduce the likelihood of fragments of the solid aerosol forming material escaping the interior chamber 66. For example, the openings 68 in the end walls 64 may have a characteristic width that is comparable to, or less than, the characteristic average smallest dimension of the fragments of solid aerosol forming material. In some examples a binder may be used to help prevent settling of the fragments within the consumable component.

Also located within the interior chamber 66 of the consumable component 4 is a heater 70 which is arranged to heat the solid aerosol forming material when supplied with power from the reusable part 2 so as to generate a vapor for user inhalation during use. As noted above, in the example of FIG. 1, power is supplied to the consumable component by electromagnetic induction. Thus, the heater 70 in the consumable component 4 comprises a material which is susceptible to electromagnetic induction, for example comprising a ferritic or martensitic steel. In this example the heater 70 is in the form of a solid rod having a diameter of around 2 mm. The heater 70 in this example is supported within the chamber 66 by its ends being located in recesses in the respective end walls, as schematically represented in FIG. 1. In other examples, the heater 70 may be mounted differently. For example the heater may be provided with one or more mounting collars which extends from the heater to the inner surface of the outer wall 62. In yet other examples, the heater may not be mounted to the outer housing at all, but may simply be held in place by the fragments of solid vapor precursor material packed around it.

To use the electronic cigarette 1 a user inserts the consumable component 4 into the consumable component receiving zone 52 through the mouthpiece opening 50. If provided, a mouthpiece cap may then be added to the mouthpiece opening end of the electronic cigarette 1. When the electronic cigarette is turned on and a user presses the input button 14, the controller circuitry 18, and in particular the power supply control circuitry 22, is configured to supply electrical power to the inductive heating coil 23 surrounding the consumable component 4 in the consumable component receiving zone 52. Electromagnetic energy is thus transferred from the heating coil 23 to the heater 70 in accordance with conventional electromagnetic heating techniques. The inductive heating coil 23 in this example comprises a helical coil wound extending along a portion of the receiving zone that surrounds the heater 70 (which in the example of FIG. 1 is most of the length of the receiving zone 52). Thus, when the consumable component 4 is received in the receiving zone 52 and the inductive heating coil 23 is driven to induce current in the heater 70, the heater is heated. The operating characteristics of the inductive heating coil 23, for example in terms of the number of turns, current and frequency of operation, may be selected having regard to the well understood principles of inductive heating taking account of the particular heater geometry adopted in a given implementation. In this regard, the inductive heater coil may, for example, be designed so as to heat the heater in the consumable component to a temperature of around 200° on a timescale on the order of a few seconds.

Heat from the heater is transferred to the solid aerosol forming material within the chamber 66 so as to vaporize a portion of the liquid aerosol precursor material absorbed therein to generate a vapor for user inhalation. As the vapor is generated in the consumable component, a user inhales on the mouthpiece opening 50 (or mouth piece attached to the mouthpiece opening). Air is thus drawn in through the air inlet 28, along the air path 30 and into the receiving zone through the receiving zone air inlet. The air then enters the consumable component 4 through the openings 68 in the end wall 64 adjacent the base of the receiving zone 52. The air then passes through the interior chamber 66 of the consumable component 4 by passing through the gaps between the fragments of solid aerosol precursor material. As the air passes through the interior chamber 66 it collects vapor generated by heating the solid aerosol precursor material as discussed above. The combined vapor and air forms a condensation aerosol which is drawn out through the openings 68 in the end wall 64 at the mouthpiece opening end of the receiving zone for subsequent user inhalation.

Thus, the electronic cigarette 1 represented in FIG. 1 may be used to generate vapor for user inhalation with a consumable component that is simpler to manufacture than liquid-based cartridges for electronic cigarettes and less prone to leakage, but which is also self-contained and simple and clean to handle and replace, and which can generate vapor more rapidly than a conventional electronic cigarette having a solid aerosol precursor material.

While the example electronic cigarette represented in FIG. 1 uses electromagnetic induction to heat the heater 70 in the consumable component 4, it will be appreciated that other implementations may adopt other approaches for heating.

Figure 2:
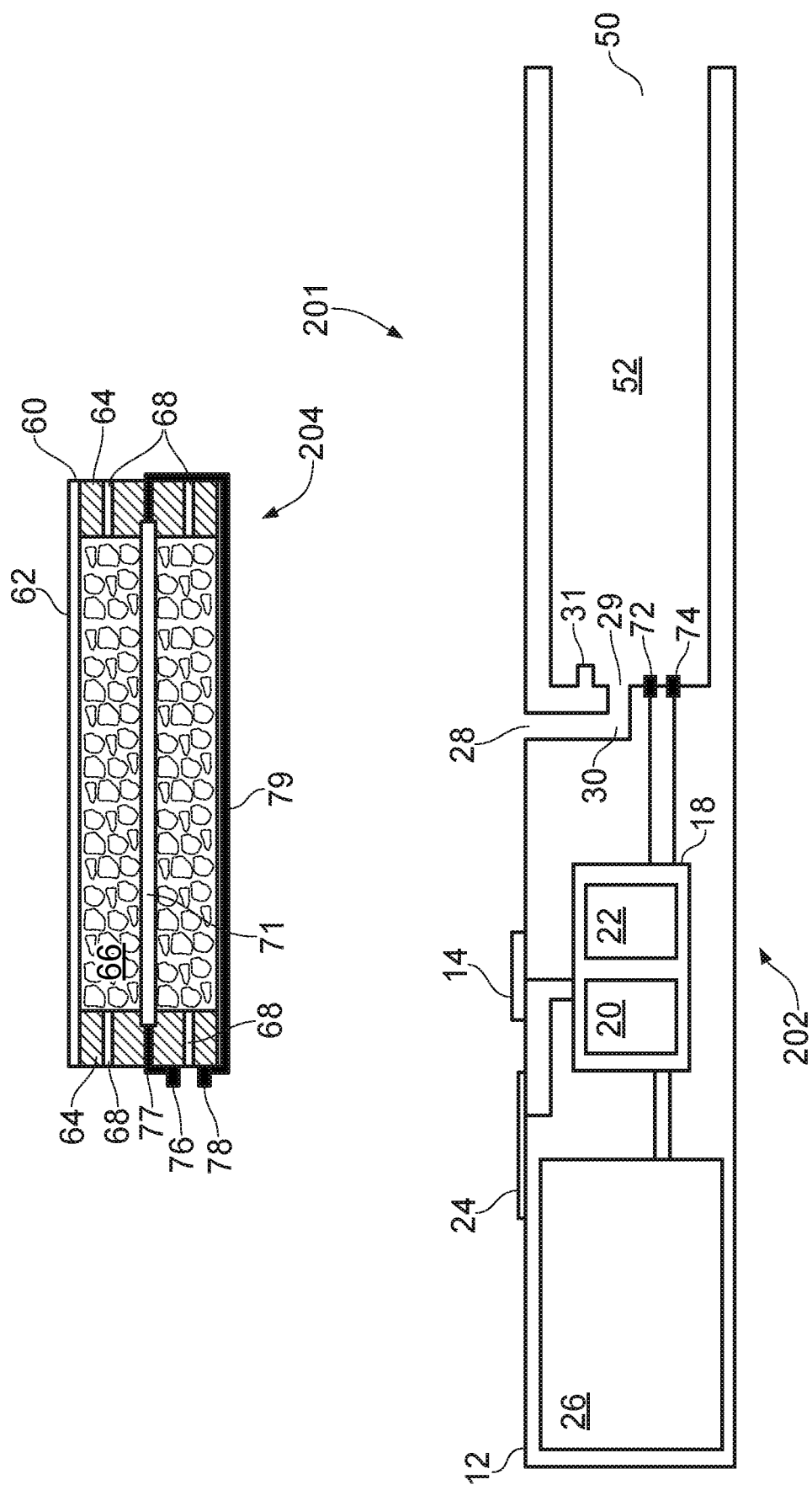
FIG. 2 is a section view of an aerosol provision system comprising a device part and a consumable component in accordance with certain other embodiments of the disclosure.

FIG. 2 is a cross-sectional view through an example e-cigarette 201 in accordance with certain embodiments of the disclosure. As with the electronic cigarette 1 represented in FIG. 1, the electronic cigarette 201 represented in FIG. 2 comprises two main components, namely a reusable part 202 and a consumable component 204. The electronic cigarette 201 represented in FIG. 2 is a variation on the electronic cigarette 1 represented in FIG. 1. Elements of the electronic cigarette 201 represented in FIG. 2 which are functionally similar to, and will be understood from, corresponding elements of the electronic cigarette 1 represented in FIG. 1 are identified with corresponding reference numerals and are not discussed again in the interests of brevity. However, the electronic cigarette 201 represented in FIG. 2 differs from the electronic cigarette 1 represented in FIG. 1 in that it does not use electromagnetic induction to transfer power from the reusable part to the consumable part, but rather uses electrical current supplied to the consumable component through direct electrical contact.

Thus, the consumable component 204 comprises a resistance heater 71 instead of an inductive heater 70 of the kind represented in FIG. 1. The heater 71 may, for example, have an overall resistance on the order of 1 or 2 Ohms and be formed from a conventional heating resistance material. The specific form of the heater may be chosen to provide the desired resistance. For example, depending on the resistivity of the material used, the heater 71 may comprise a solid rod similar to the inductive reheated heater 70 in the consumable component 4 represented in FIG. 1, or may comprise a wire wound around an electrically insulating substrate. Respective ends of the heater 71 are connected by electrical leads 77, 79 to respective ones of a pair of electrodes 76, 78 mounted on one of the end walls 64. When the consumable component 204 is located in the receiving zone 52 in the reusable part 202 of the electronic cigarette 201, the electrodes 76, 78 on the consumable component align with, and contact, corresponding electrodes 72 and 74 in the receiving zone.

To use the electronic cigarette 201 a user inserts the consumable component 204 into the consumable component receiving zone 52 through the mouthpiece opening 50. If provided, a mouthpiece cap may then be added to the mouthpiece opening end of the electronic cigarette 201. When the electronic cigarette is turned on and ready for use, the user presses the input button 14 and the controller circuitry 18, and in particular the power supply control circuitry 22, is configured to supply electrical power to the heater 71 via the electrodes 72, 74 in the receiving zone and the electrodes 76, 78 on the consumables component 204. Thus, when the consumable component 4 is received in the receiving zone 52 and power is supplied to the heater by the power supply control circuitry via the respective electrodes and connecting leads, the heater is heated. The operating characteristics of the power supplied, for example in terms of voltage and any pulse width/frequency modulation scheme applied, may be selected having regard to the well understood principles of resistance heating in electronic cigarettes. In this regard, the power supply control circuitry may, for example, be designed so as to supply power (current) to the heater so as to heat the heater to a temperature of around 200° on a timescale on the order of a second.

Heat from the heater 71 is transferred to the solid aerosol forming material within the chamber 66 so as to vaporize a portion of the liquid aerosol precursor material absorbed therein to generate a vapor for user inhalation in the same manner as discussed above for the electronic cigarette 1 represented in FIG. 1.

Figure 3:
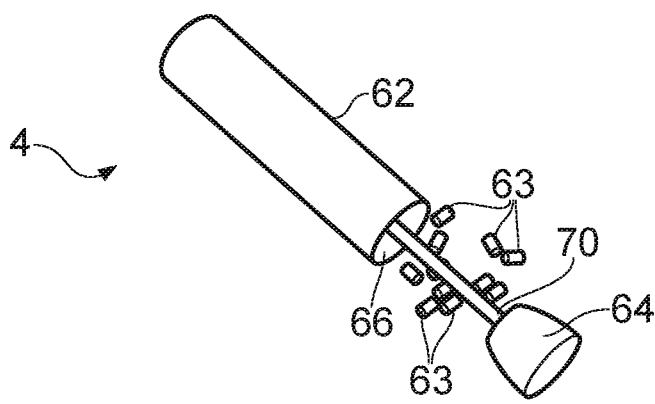
FIG. 3 is a perspective view of a consumable component in accordance with certain embodiments of the disclosure.

FIG. 3 is a schematic perspective view of the consumable component 4 for the electronic cigarette 1 represented in FIG. 1 in a partially disassembled state. From this it can be seen in this example the fragments of solid aerosol precursor material 63 are fairly regular in shape and each have a generally cylindrical form with a length of around 2 mm and a diameter of around 1 mm. These may be formed, for example, by extrusion, i.e. by cutting lengths from an extruded cylinder. As noted above, other forms of solid aerosol precursor material may be used, such as irregular fragments or regular fragments of other shapes, for example spherical shapes, and, furthermore may in other examples comprise cut/shredded tobacco or other sheet material, such as paper.

Figure 4A:
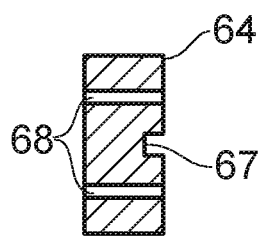
FIG. 4A is a section view of an end wall for a consumable component in accordance with certain embodiments of the disclosure.
Figure 4B:
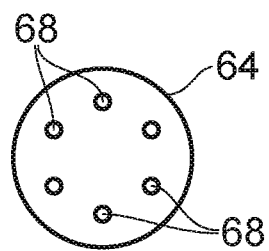
FIG. 4B is an end view of the end wall of FIG. 4A.
Figure 4C:
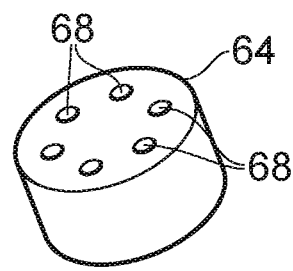
FIG. 4C is a perspective view of the end wall of FIG. 4A.

FIGS. 4A to 4C are respective cross-section, face and perspective views of an end wall 64 of the kind used in the consumable components 4, 204 of the electronic cigarettes 1, 201 represented in FIGS. 1 and 2. As noted above, the end wall comprises a ceramic material and may be formed in accordance with conventional techniques. The end wall in this example comprises six openings 68 arranged around a circle around halfway between the centre and the edge of the end wall 64. However, in some example implementations the openings in an end wall may be more tightly packed around a location in the end wall where the heater is mounted, i.e. in this example the central part of the end wall. This can help reduce thermal conduction between the heater and the outer parts of the end wall/outer housing of the consumable component. Also apparent in FIG. 4A is a recess 67 dimensions to receive an end of the heater 70, 71 as discussed above.

Figures 4D, 4E, 4F, 4G:
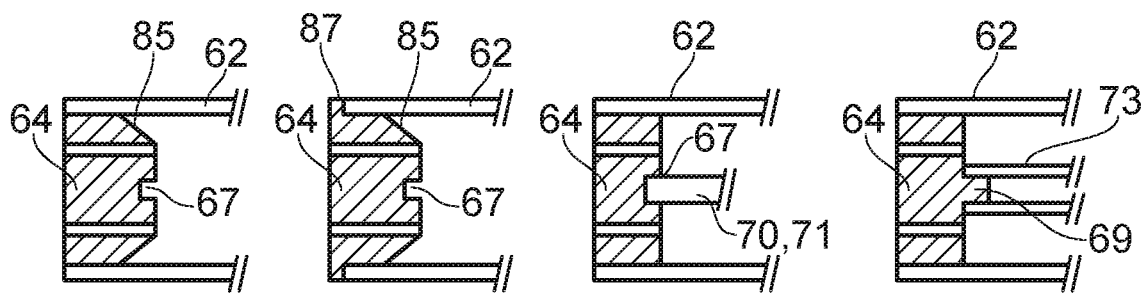
FIG. 4D is a section view of an end wall in accordance with certain other embodiments of the disclosure.
FIG. 4E is a section view of an end wall in accordance with certain other embodiments of the disclosure.
FIG. 4F is a section view of an end wall in accordance with certain other embodiments of the disclosure.
FIG. 4G is a section view of an end wall in accordance with certain other embodiments of the disclosure.

FIGS. 4D to 4G are cross-section views representing variations of the end wall 64 shown in FIGS. 4A to 4C in accordance with various embodiments of the disclosure. In the example of FIG. 4D, the end wall 64 is provided with a chamfer 85 to facilitate insertion into the outer housing 62 during assembly. In the example of FIG. 4E, the end wall 64 is provided with a chamfer 85 to facilitate insertion into the outer housing 62 during assembly and a flange/lip 87 arranged to abut the end of the outer housing 62 when the end wall 64 is properly inserted. The example of FIG. 4F shows in more detail how an end of the heater 70, 71 may be received in a recess 67 of the end wall 64 to provide physical support for the heater 70, 71. FIG. 4G shows an example in which the end wall 64 is provided with a protruding boss 67, rather than a recess 67, to support a heater 73, which in this example comprises a tubular portion into which the protruding boss 69 is inserted to support the heater 73. It will, of course, be appreciated that different aspects of the different examples represented in FIG. 4A to 4G may be combined with other aspects of these examples, for example, an end wall of the kind represented in FIG. 4G may be provided with a chamfer 85 and/or a flange 87 of the kind represented in FIG. 4E and so forth.

Figures 5A, 5B, 5C, 5D, 5E:
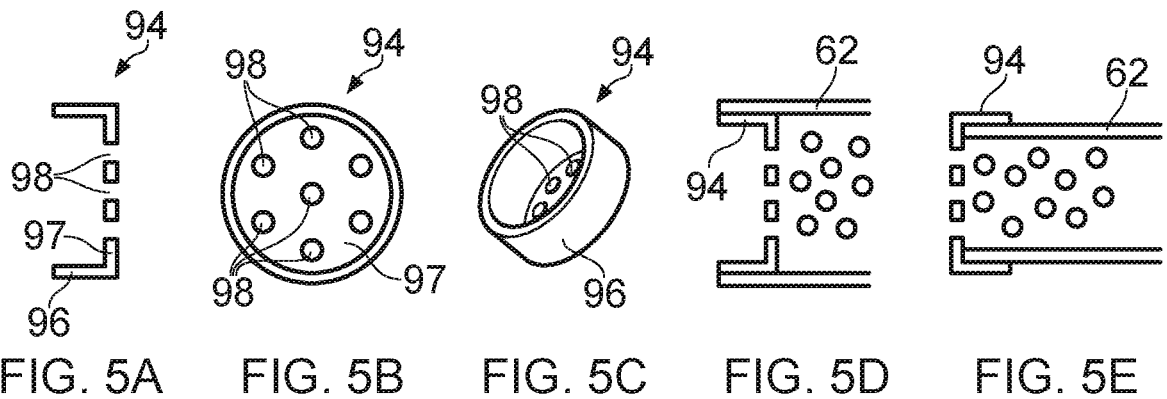
FIG. 5A is a section view of an end wall for a consumable component in accordance with certain other embodiments of the disclosure.
FIG. 5B is an end view of the end wall of FIG. 5A.
FIG. 5C is a perspective view of the end wall of FIG. 5A.
FIG. 5D is a section view illustrating the coupling of the end wall of FIG. 5A and a tubular outer wall in accordance with certain embodiments of the disclosure.
FIG. 5E is a section view illustrating the coupling of the end wall of FIG. 5A and a tubular outer wall in accordance with certain other embodiments of the disclosure.

FIGS. 5A to 5C schematically represent respective cross-section, face and perspective views of an alternative form of end wall 94 for use in a consumable component of the kind represented in FIGS. 1 and 2 in accordance with other examples of the disclosure. Whereas the end walls 64 discussed above with reference to FIGS. 1 to 4 are formed of a ceramic material, the end wall 94 represented in FIGS. 5A to 5C is formed from card and comprises a circular face 67 comprising openings 98 for allowing air into the consumable component and a sidewall portion 96 arranged to couple the end wall 98 to the outer housing 62 of the consumable component, e.g. by a friction fit. The end wall 98 may be coupled to the tubular outer wall 62 of a consumable component by being inserted, e.g. face first, in the manner of a plug, as schematically shown in the cross-section representation in FIG. 5D, or may be placed over the tubular outer wall 62 of a consumable component in the manner of a cap, as schematically shown in the cross-section representation in FIG. 5E. In either case the end wall may be retained by a friction fit, or other means, for example using an adhesive. The heater in a consumable component using an end wall of the kind represented in FIGS. 5A to 5C may be mounted to the end wall, for example by passing through an opening in the end wall, or might not be mounted to the end wall. For the examples represented in FIGS. 5A to 5E it is assumed the heater is not mounted to the end wall, and instead the end wall has an additional opening 98 towards the centre of the end face 97.

Figure 6:
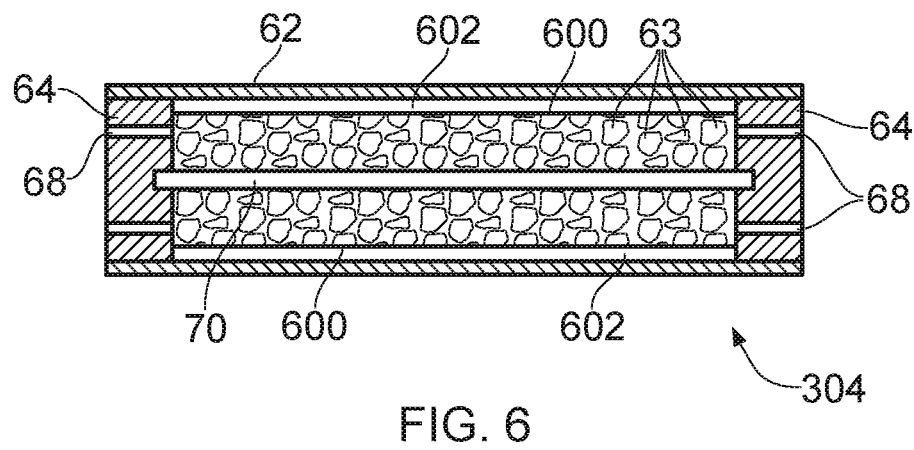
FIG. 6 is a section view of a consumable component in accordance with certain embodiments of the disclosure.

FIG. 6 schematically represents in cross-section view a consumable component 304 which is a variation on that represented in FIG. 1. Elements of the consumable component 304 represented in FIG. 6 which are functionally similar to, and will be understood from, corresponding elements of the consumable component 4 represented in FIG. 1 are identified with corresponding reference numerals and are not discussed again in the interests of brevity. However, the consumable component 304 represented in FIG. 6 differs from the consumable component 4 represented in FIG. 1 by having a secondary wall 600 arranged within the outer housing 62 so as to define an air gap 602 between the outer housing 62 and the secondary wall 600. The secondary wall 600 may be formed of the same, or a different, material to the outer housing 62. The fragments of solid aerosol precursor material 63 are retained by the secondary wall 600 and the end walls 64. The presence of the air gap 602 can help prevent the outer wall 62 becoming undesirably hot during use in situations where this is considered a potential concern.

Figure 7:
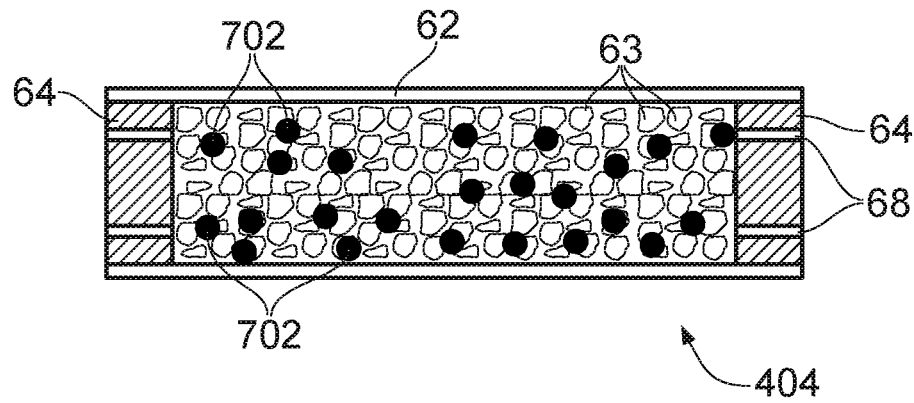
FIG. 7 is a section view of a consumable component in accordance with certain embodiments of the disclosure.

FIG. 7 schematically represents in cross-section view a consumable component 404 which is another variation on that represented in FIG. 1. Elements of the consumable component 404 represented in FIG. 7 which are functionally similar to, and will be understood from, corresponding elements of the consumable component 4 represented in FIG. 1 are identified with corresponding reference numerals and are not discussed again in the interests of brevity. The consumable component 404 represented in FIG. 7 differs from the consumable component 4 represented in FIG. 1 in that rather than contain a heater in the form of a central rod, the heater in the example of FIG. 7 comprises a distributed arrangement of metallic bodies/particles 702 which are susceptible to electromagnetic induction heating. During use these metallic bodies/particles are heated by induced electromagnetic currents in a corresponding manner to that discussed above with reference to FIG. 1. The distributed particles can provide for more distributed heating throughout the chamber containing the fragments of solid aerosol forming material.

Other forms of heater may be used in other implementations.

Figure 8A:
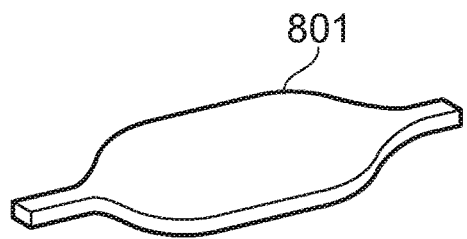
FIG. 8A is a perspective view of a heater for consumable components in accordance with certain embodiments of the disclosure.

For example, FIG. 8A schematically represents in perspective view a heater 801 having a generally planar form but with cylindrical endpoints for mounting. In some respects this may be considered to correspond to a flattened form of a rod of the kind discussed above with reference to FIGS. 1 and 2.

Figure 8B:
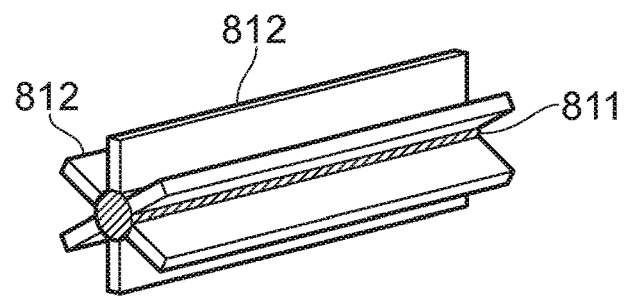
FIG. 8B is a perspective view of a heater for consumable components in accordance with certain other embodiments of the disclosure.

FIG. 8B schematically represents in perspective view a heater 811 which has the form of a rod similar to the heater is 70, 71 discussed above with reference to FIGS. 1 and 2, but further comprises vanes 812 which are attached to the heater 811 and which extend out to the inner wall of the outer housing of a consumable component so as to support the heater 811 without mounting to the end walls.

Figure 8C:
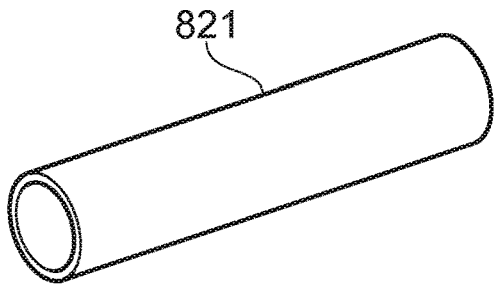
FIG. 8C is a perspective view of a heater for consumable components in accordance with certain other embodiments of the disclosure.

FIG. 8C schematically represents in perspective view a heater 821 having a generally tubular form. Such a heater may, for example, be mounted to an end wall in the manner represented in FIG. 4G.

It will be appreciated the heaters represented in FIGS. 8A to 8C may be formed from materials similar to those discussed above for the heater is 70, 71 represented in FIGS. 1 and 2, i.e. from materials susceptible to magnetic induction/resistive heating according to the manner of energy transfer.

Figure 9:
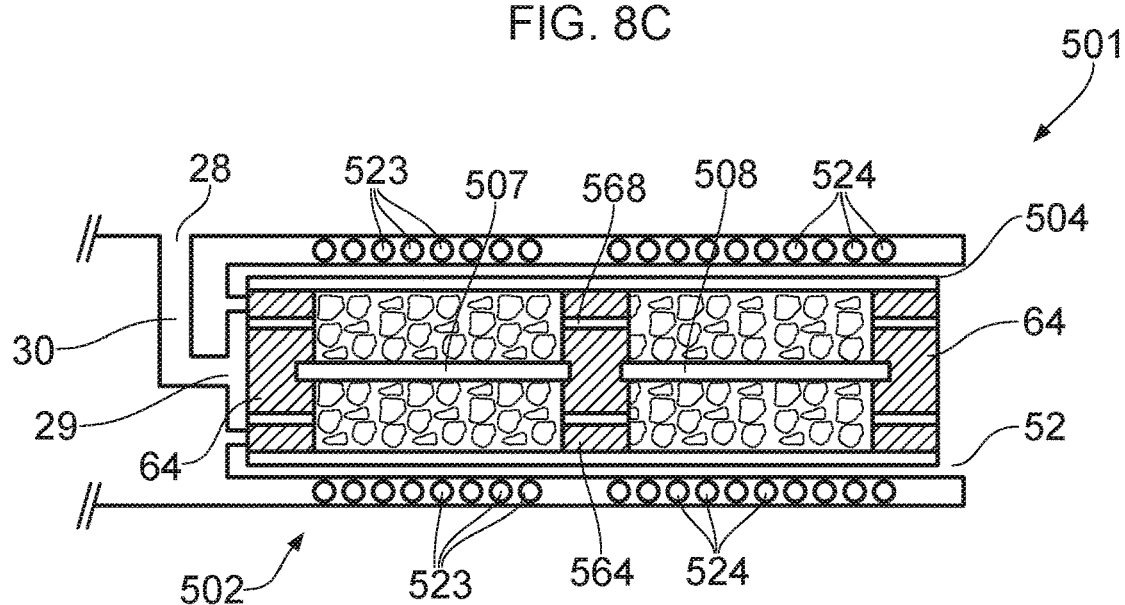
FIG. 9 is a section view illustrating a receiving section/zone portion of a device part and a consumable component in accordance with certain embodiments of the disclosure.

FIG. 9 is a cross-sectional view through a part of an example e-cigarette 501 in accordance with certain embodiments of the disclosure. As with the electronic cigarette 1 represented in FIG. 1, the electronic cigarette 502 represented in FIG. 2 comprises two main components, namely a reusable part 502 and a consumable component 504. In FIG. 9 only a portion of the reusable part 502 in the vicinity of its receiving zone is shown with the consumable component 504 in place for use (i.e. in the receiving zone). The electronic cigarette 501 represented in FIG. 9 is a variation on the electronic cigarette 1 represented in FIG. 1. Elements of the electronic cigarette 501 represented in FIG. 9 which are functionally similar to, and will be understood from, corresponding elements of the electronic cigarette 1 represented in FIG. 1 are identified with corresponding reference numerals and are not discussed again in the interests of brevity. However, the electronic cigarette 501 represented in FIG. 9 differs from the electronic cigarette 1 represented in FIG. 1 in that the interior chamber of the consumable component 504 is divided into two sections (zones) by a central wall 564. Each section of the interior chamber contains fragments/elements of solid aerosol precursor material and a respective heater 507, 508, such as those discussed above with reference to FIG. 1. The central wall 564 may, for example, be formed in the same way as the end walls 64. The central wall 564 includes openings 568 to allow air to flow through the central wall during inhalation. The reusable part 502 comprises a first induction heating coil 523 and a second induction heating coil 524 which may be independently driven to induce electric currents, and so heat, respective ones of the heaters 507, 508. Thus the electronic cigarette 501 represented in FIG. 9 differs from that represented in FIG. 1 by virtue of having two separate chambers that may, for example, contain different aerosol precursor materials and which may be independently heated to generate vapor with different characteristics, for example different flavors and/or relative amount of nicotine. It will be appreciated in other example implementations there may be more than two separate chambers in a consumable component. Furthermore, the different chambers may in some implementations contain the same aerosol precursor materials and be provided so that different uses of the device can begin with a "fresh" portion of consumable material for each session of use. It will be appreciated that in some implementations there may be no walls dividing the different zones of aerosol forming material, and instead a single heater may run the length of the consumable component through multiple notional zones, with localized heating of the heater provided by suitably arranged induction coils which can be selectively activated at different locations along the length of the heater (for example as schematically shown did in FIG. 9).

Figure 10:
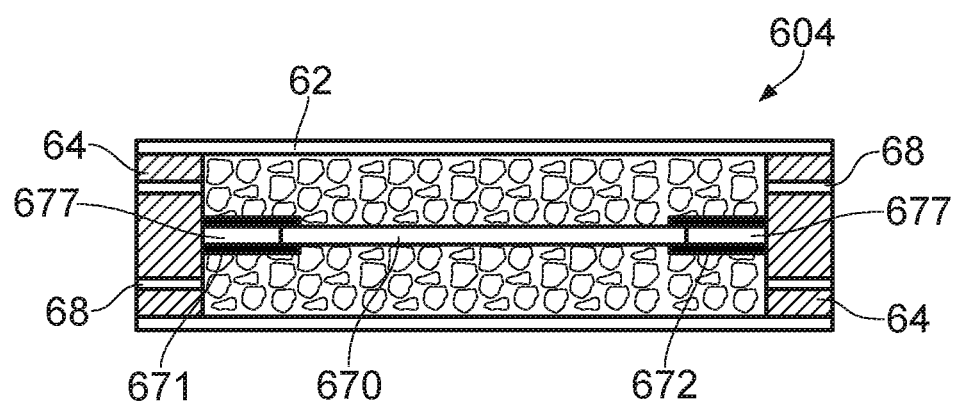
FIG. 10 is a section view of a consumable component in accordance with certain embodiments of the disclosure.

FIG. 10 schematically represents in cross-section view a consumable component 604 for use in an electronic cigarette according to certain other embodiments of the disclosure. This consumable component may, for example, be used in conjunction with the reusable component of the electronic cigarette represent in FIG. 1. The consumable component 604 represented in FIG. 10 is in many respects similar to, and will be understood from, the other consumable components discussed above and elements of the consumable component 604 represented in FIG. 10 which are functionally similar to, and will be understood from, corresponding elements of the other consumable components discussed herein are identified with corresponding reference numerals and are not discussed again in the interests of brevity. The consumable component 604 in FIG. 10 differs from the consumable component 4 in FIG. 1 in having a shorter heater 670 which is not mounted directed to the end walls 64, but is instead mounted via intervening thermal insulating elements, such as ceramic tubing, 671, 672. In this example configuration the thermal insulating elements are mounted on posts 677 protruding from the respective end walls. This arrangement can help reduce the amount of heat transferred to the end walls 64 in implementations where this is a concern.

Figure 11:
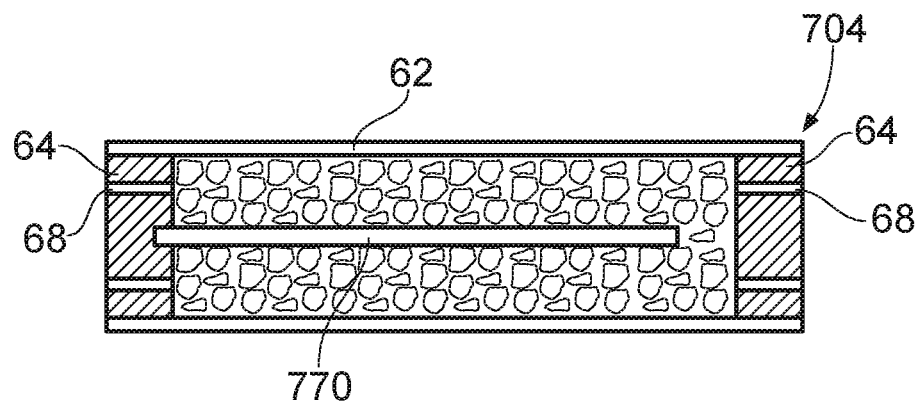
FIG. 11 is a section view of a consumable component in accordance with certain other embodiments of the disclosure.

FIG. 11 schematically represents in cross-section view a consumable component 704 for use in an electronic cigarette according to certain other embodiments of the disclosure. This consumable component may, for example, be used in conjunction with the reusable component of the electronic cigarette represent in FIG. 1. The consumable component 704 represented in FIG. 11 is in many respects similar to, and will be understood from, the other consumable components discussed above and elements of the consumable component 704 represented in FIG. 11 which are functionally similar to, and will be understood from, corresponding elements of the other consumable components discussed herein are identified with corresponding reference numerals and are not discussed again in the interests of brevity. The consumable component 704 in FIG. 11 differs from the consumable component 4 in FIG. 1 in having a shorter heater 770 which is mounted at only one end to one of the end walls 64. This arrangement can help reduce the amount of heat transferred to the other end wall, in implementations where this is considered a concern, for example if an end wall that protrudes from the electronic cigarette would be expected to become particularly hot during normal use if it were in contact with the heater.

Thus, a range of different arrangements of electronic cigarettes have been described. It will, however, be appreciated there are many modifications and variations that can be made to the above-described examples in other implementations. For example, whereas in the above-described examples the electronic cigarettes have comprised a button for manual activation of power supplied to the heater in the consumable component, other example implementations may include a puff detector, for example in the form of a pressure sensor coupled to an air path through the electronic cigarette, configured to trigger the supply of power to the heater automatically in response to user inhalation.

In other examples, an electronic cigarette in accordance with the principles described herein may additionally comprise a temperature sensor for monitoring the temperature of the heater. This may be used, for example, to allow the temperature of the heater to be regulated during use. The temperature sensor may, for example, be mounted in the consumable component itself, for example a thermistor, with appropriate connection to the reusable component, or the sensor may be remote from the consumable component. For example the temperature sensor may be an infrared radiation sensor arranged to detect heat from the consumable component.

In some examples, some of the functionality of the elements discussed above may be provided by a single element. For example, in one configuration a consumable component may be provided with a metallic outer housing which both retains the fragments of solid aerosol forming material and act as a heater (inductive or resistive).

In some example implementations the consumable component may comprise the only source of vapor precursor/forming material for the aerosol provision system/electronic cigarette. That is to say, in some cases the consumable component does not in effect correspond with an additional insert, for example for use as a flavor modifier in an electronic cigarette that also comprises a vaporizer for heating a liquid formulation, but is the main source of vapor for the electronic cigarette.

Thus, there has been described a consumable component for an aerosol provision system comprising: an outer housing comprising an outer wall extending between first and second end walls to define an interior chamber; a plurality of elements of solid aerosol forming material for generating an aerosol for user inhalation when heated, wherein the plurality of elements of solid aerosol forming material are retained within the interior chamber by the housing and wherein the first and second end walls comprise openings to allow air to flow into the interior chamber through the first end wall and out of the interior chamber through the second end wall during use, and a heater located within the interior chamber and configured to heat the elements of solid aerosol forming material during use to generate a vapor for user inhalation.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A consumable component for an aerosol provision system comprising:
    an outer housing comprising an outer wall extending between a first end wall and a second end wall to define an interior chamber;
    a plurality of elements of solid aerosol forming material for generating an aerosol for user inhalation, wherein the plurality of elements of solid aerosol forming material are retained within the interior chamber by the housing and wherein the first end wall and the second end wall comprise openings to allow air to flow into the interior chamber through the first end wall and out of the interior chamber through the second end wall during use; and
    a heater located within the interior chamber and configured to heat the plurality of elements of solid aerosol forming material during use to generate a vapor for user inhalation.

2. The consumable component of claim 1, wherein the plurality of elements of solid aerosol forming material comprise elements of a solid substrate material holding a liquid aerosol precursor material.

3. The consumable component of claim 1, wherein the plurality of elements of solid aerosol forming material comprise tobacco.

4. The consumable component of claim 1, wherein the plurality of elements of solid aerosol forming material comprise calcium carbonate.

5. The consumable component of claim 1, wherein an average characteristic dimension for the plurality of elements of solid aerosol forming material is more than 1 mm.

6. The consumable component of any claim 1, wherein an average characteristic dimension for the plurality of elements of solid aerosol forming material is less than 5 mm.

7. The consumable component of claim 1, wherein the heater comprises an inductive susceptor configured to be inductively heated.

8. The consumable component of claim 1, wherein the heater comprises a resistance heater, and wherein the consumable component further comprises electrical contacts on the outer housing electrically connected to the resistance heater.

9. The consumable component of claim 1, wherein at least a part of the heater has at least one of:
　a planar form,
　a tubular form,
　a rod-shaped form, or
　comprises a plurality of electrically conductive elements distributed through the plurality of elements of solid aerosol forming material.

10. The consumable component of claim 1, wherein the heater is mounted to at least one of the first end wall or the second end wall.

11. The consumable component of claim 1, wherein at least one of the first end wall or the second end wall comprises a cap fitted over an end of the outer wall or a plug fitted into an end of the outer wall.

12. The consumable component of claim 1, wherein at least a portion of the outer housing comprises at least one of: a paper material, a card material, a tobacco material, a ceramic material, a metallic material, a carbon material, or a plastics material.

13. The consumable component of claim 1, wherein the plurality of elements of solid aerosol forming material are arranged into different zones within the consumable component and wherein the heater is configured to selectively independently heat elements of the plurality of elements of solid aerosol forming material in the different zones.

14. An aerosol provision system for generating a vapor, the aerosol provision system comprising:
　the consumable component of claim 1;
　a consumable component receiving section for removably receiving the consumable component for use; and
　a power source for selectively supplying power to the heater in the consumable component to generate vapor from the solid aerosol forming material for user inhalation.

15. The aerosol provision system of claim 14, wherein the aerosol provision system further comprises electrical contacts for supplying power to the heater in the consumable component via corresponding electrical contacts on the housing of the consumable component.

16. The aerosol provision system of claim 14, wherein the aerosol provision system further comprises an induction heating coil for inductively supplying power to the heater.

17. The aerosol provision system of claim 14, wherein the aerosol provision system further comprises a sensor for measuring a temperature associated with the consumable component during use.

18. The aerosol provision system of claim 14, wherein the consumable component comprises a sole source of vapor precursor material for the aerosol provision system.

19. Consumable component means for an aerosol provision system comprising:
　outer housing means comprising outer wall means extending between first end wall means and second end wall means to define an interior chamber;
　a plurality of elements of solid aerosol forming means for generating an aerosol for user inhalation, wherein the plurality of elements of solid aerosol forming means are retained within the interior chamber by the housing means and wherein the first end wall means and the second end wall means comprise opening means to allow air to flow into the interior chamber through the first end wall means and out of the interior chamber through the second end wall means during use, and
　heater means located within the interior chamber and configured to heat the plurality of elements of solid aerosol forming means during use to generate a vapor for user inhalation.

* * * * *